United States Patent [19]

Penneck

[11] 3,983,070

[45] Sept. 28, 1976

[54] POLYMERIC ADHESIVE

[75] Inventor: Richard John Penneck, Lechlade, England

[73] Assignee: Raychem Corporation, Menlo Park, Calif.

[22] Filed: Apr. 24, 1973

[21] Appl. No.: 354,128

Related U.S. Application Data

[63] Continuation-in-part of Ser. No. 273,991, July 21, 1972, abandoned.

[30] Foreign Application Priority Data

Apr. 28, 1972 United Kingdom............. 19780/72

[52] U.S. Cl. ................................ 260/38; 156/332; 156/334; 260/37 R; 260/42.15
[51] Int. Cl.² .......................................... C08K 9/06
[58] Field of Search................ 260/41, 80.8, 42.15, 260/38 R, 37 R

[56] References Cited

UNITED STATES PATENTS

| | | | |
|---|---|---|---|
| 3,290,267 | 12/1966 | Vanderbilt et al.................... | 260/41 |
| 3,620,878 | 11/1971 | Guthrie............................... | 156/309 |
| 3,691,120 | 9/1972 | Susuki et al. ........................ | 260/41 |

FOREIGN PATENTS OR APPLICATIONS

| | | | |
|---|---|---|---|
| 680,105 | 2/1964 | Canada............................. | 260/80.8 |
| 1,284,082 | | United Kingdom | |
| 1,303,432 | 1/1973 | United Kingdom | |

OTHER PUBLICATIONS

Union Carbide Silones, Union Carbide Corp., SF-1160B New York, N.Y., Aug. 1966, pp. 4 & 14.
Modern Plastics Encyclopedia, 1967, Sept. 1966, vol. 44, No. 1A, pp. 416–417.

*Primary Examiner*—James H. Derrington
*Attorney, Agent, or Firm*—Lyon and Lyon

[57] ABSTRACT

This invention relates to adhesives which are particularly useful in bonding polymeric materials used in the encapsulation and termination of insulated electrical conductors. The adhesive comprises a polar copolymer of an α-olefin, said copolymer preferably having an acid number in the range of from 4 to 40 and containing pendant ester, amide, ketonic, anhydride or carboxylic acid groups and an inorganic silicon-containing compound which has been chemically treated with an organosilicon compound.

18 Claims, No Drawings

POLYMERIC ADHESIVE

This application is a continuation-in-part of my copending application entitled "Improvements In and Relating to Polymer Compositions", Ser. No. 273,991, filed July 21, 1972 now abandoned in favor of continuation-in-part Ser. No. 540,447, filed Jan. 13, 1975.

This invention relates to adhesives for use in encapsulation and termination of electrical conductors such as electrical cables. In carrying out encapsulation, termination or repair of such electrical cables, it is often desirable to bond a polymeric material to another polymeric material or to some other substrate. It is important that a high bond strength be obtained. The present invention relates to an adhesive which provides a high bond strength and possesses desirable electrical characteristics.

The present invention provides an adhesive comprising
a. a polar copolymer of an $\alpha$-olefin, and
b. a chemically-treated silica filler, as hereinafter defined.

The present invention also provides an article comprising two or more members bonded together by the above adhesive.

The polar $\alpha$-olefin copolymer advantageously has an acid number in the range of from 4 to 40, high acid number in the range of from 20 to 40, especially about 30, being preferred. Typical polar $\alpha$-olefin copolymers, ethylene-based materials being preferred, contain pendant ester, amide, ketonic, anhydride or carboxylic acid groups.

Amongst suitable materials there may especially be mentioned:
1. Ethylene/vinyl acetate/carboxylic acid terpolymers where the acid may be, for example, acrylic acid, methacrylic acid, itaconic acid, etc.
2. Ethylene/olefinically, preferably ethylenically, unsaturated carboxylic acid and/or ester copolymers, e.g. ethylene/acrylic acid, ethylene/methacrylic acid, ethylene/ethyl acrylate, ethylene/ethyl itaconate, ethylene/ethyl maleate, ethylene/ethyl fumarate and copolymers of ethylene with the corresponding methyl esters, etc.
3. Ethylene/vinyl ester copolymers, e.g. ethylene/vinyl acetate.
4. Polyolefin polymers and copolymers to which have been grafted polymers of maleic acid or anhydrides, esters or amides thereof.
5. Graft copolymers of $\alpha$-olefins with fumaric acid or anhydrides, esters or amides thereof.
6. Any of the above materials having additional di or polycarboxylic acids compounded into the polymer in accordance with the disclosure of U.S. Pat. No. 3,620,878, the disclosure of which is incorporated herein by reference. Suitable acids include terephthalic acid, pyromellitic acid, benzophenone tetracarboxylic acid, etc. The acids are generally incorporated in amounts in the range of from 1 to 15% by weight of the polymer.

It will be appreciated that mixtures of two or more polar $\alpha$-olefin copolymers can be used. This may be desirable in some cases, e.g., to obtain preferred flow properties for the adhesive. Other polymeric materials can be incorporated into the adhesive to assist in obtaining desired flow properties. Especially suitable in this respect are the polycaprolactone polymers sold by Union Carbide under the names PCL-300 and PCL-700, the latter being preferred in an amount of about 5 to 20 percent by weight and preferably about 10 per cent.

The $\alpha$-olefin copolymer is advantageously based on ethylene and vinyl acetate, copolymers containing up to 20% by weight especially about 10% by weight, of vinyl acetate being preferred. Especially useful is an ethylene (83%)/vinyl acetate (12%)/methacrylic acid (5%) terpolymer sold commercially by duPont under the name Elvax 3689.3. This has a low MFI of approximately 3.0 and a high acid number of about 30.

The chemically treated silica filler is a filler comprising an inorganic silicon-containing compound containing the Si-O-Si group which has been treated with one or more organic silicon compounds. Such chemically treated silica fillers and their preparation and properties are fully described in British Patent Specification No. 1,284,082, the disclosure of which is incorporated herein by reference.

They are silicas or metal silicates, e.g. aluminium silicate, magnesium silicate, calcium silicate, calcium aluminium silicate, having a specific surface area, measured by the BET nitrogen absorption method, of at least 50 m$^2$/g, preferably at least 100 m$^2$/g, which have been treated with one or more silanes, e.g. as listed in British Patent Specification No. 1,284,082, and/or with other organosilicon compounds such as octamethyltetracyclosiloxane, tetramethylcyclosiloxane, etc. The inorganic silicon-containing compound may be anhydrous (3.5% bound H$_2$O), hydrated or an aerogel (prepared, for example, as described in Bachman et al, Rubber Reviews 1959, issue of Rubber and Chemistry and Technology). The inorganic filler is advantageously coated with the organosilicon compound at least to the extent of one monolayer, although fillers coated to a lesser extent may also be used.

Trimethyl chlorosilane is a preferred treating agent. An especially useful chemically treated silica filler is Aerosil R972 which is a silica having a specific surface area of about 200 m$^2$/g and coated with trimethylchlorosilane.

The treated silica filler is advantageously used in an amount of up to 20%, preferably in the range of from 3 to 10%, by weight based on the total weight of the adhesive composition.

The adhesive compositions of the present invention are especially suitable for use in the encapsulation and termination of insulated electrical cables, especially when heat-recoverable materials are used to effect the encapsulations and terminations. We have surprisingly found that the incorporation of the treated silica filler substantially increases the strength of the bonds obtained between the cross-linked polyethylene used for insulation and the lead sheaths of the cables. Furthermore, high peel strengths are obtained even at temperatures as high as 70°C.

Thus the adhesives of the present invention are especially useful as inside coatings for the heat-shrinkable sleeves and end caps new widely used for cable joints and termination, especially for telephone cables. For this reason, the $\alpha$-olefin copolymer used advantageously has a low melt flow index before compounding, preferably of less than 5.

The adhesives may include other additives such, for example, as pigments, antioxidants and processing aids, etc. Adhesion promotors, for example, silanes and partially hydrolysed silanes, and tackifying resins, for example phenol/aldehyde reaction products and ketone-/aldehyde reaction products, may also be incorporated.

The following Examples illustrate the invention, parts and percentages being by weight unless otherwise stated. Peel bond strengths are given throughout in pounds force per linear inch width.

EXAMPLE 1

The following mixes were blended on a laboratory 2 roll mill at a temperature of 110°C.

| Formulation No. | 1 | 2 |
|---|---|---|
| Elvax 3689.3 | 150 | 150 |
| Agerite Resin D (antioxidant) | 3 | 3 |
| Partially hydrolysed A1111 from Union Carbide (adhesion promoter - N-bis 2-hydroxyethyl-3-aminopropyl triethoxysilane) | 2.4 | 2.4 |
| Aerosil R972 (chemically treated silica filler) | — | 10 |

After compounding, each formulation was chipped and extruded into a film 1 inch wide and 0.012 ins. thick using the following temperature profile: 100°C - head temperature and 90°C - barrel temperature.

These adhesives were used to bond 2 different types of crosslinked polyethylenes (see table). The peel joints were prepared by interleaving the adhesive between 1 inch wide strips of the crosslinked polyethylenes, with a 5 lb. weight on it, this giving a bond line pressure of 5 p.s.i. The joints were heated at 150°C for 20 mins. and after cooling to room temperature were left at that temperature overnight. Additional joints were made between crosslinked low density polyethylene and lead, and similarly between crosslinked medium density polyethylene and lead and between lead and lead. The peel strengths were then tested at 70°C in an Instron Tensile tester.

| | Substrates | | | | |
|---|---|---|---|---|---|
| Formulation No. | Crosslinked low density polyethylene | Crosslinked medium density polyethylene | Crosslinked low density polyethylene/lead | Crosslinked medium density polyethylene/lead | lead/lead |
| 1 | 20 | 20 | 4.2 | 1.5 | 4.9 |
| 2 | 17 | 46* | 8.4 | 6.0 | 10.0 |

*Sample still intact — it pulled out of the jaws of the Instron tester at this load.

Further comparisons were made using the formulations below.

| Formulation No. | 3 | 4 | 5 | 6 | 7 |
|---|---|---|---|---|---|
| Elvax 3689.3 | 150 | 150 | 150 | 150 | 150 |
| Agerite Resin D | 3 | 3 | 3 | 3 | 3 |
| Partially hydrolysed A1111 | 2.4 | 2.4 | 2.4 | 2.4 | 2.4 |
| Aerosil 200 (fine particle size silica filler, non-treated, specific surface area approximately 200 m²/g) | 10 | 25 | — | — | — |
| Vulcan 3 (fine particle size carbon black) | — | — | 10 | 25 | — |
| China Clay | — | — | — | — | 10 |

The following results were obtained.

| | Substrates | |
|---|---|---|
| Formulation No. | Crosslinked medium density polyethylene | Crosslinked medium density polyethylene/lead |
| 3 | 34.5 | 3.0 |
| 4 | 30.5 | 3.2 |
| 5 | 29.5 | 3.8 |
| 6 | 29.5 | 4.2 |
| 7 | — | 0.88 |

The above results clearly demonstrate the improvements in bond strength obtained with the use of the treated silica filler in accordance with the present invention (Formulation 2).

EXAMPLE 2

| Formulation No. | 8 | 9 | 10 |
|---|---|---|---|
| Elvax 3689.3 | 234 | 234 | 234 |
| Agerite Resin D | 1.2 | 1.2 | 1.2 |
| PCL-700 (polycaprolactone ex Union Carbide) | 23.4 | 23.4 | 23.4 |
| Aerosil R972 | — | 15.6 | — |
| Aerosil 200 (uncoated) | — | — | 15.6 |

These adhesives were prepared as described and were used to bond crosslinked medium density polyethylene to itself and to lead. The following peel strengths were obtained.

| | Substrates | | |
|---|---|---|---|
| Formulation No. | XL medium density polyethylene | | XL medium density polyethylene/lead |
| | Room temp. | 70°C | 70°C |
| 8 | 39 | 18.1 | 1.9 |
| 9 | 72 | 43.4 | 9.1 |
| 10 | 34 | 9.8 | 1.5 |

EXAMPLE 3

This Example illustrates the use of various treated silica fillers.

| Formulation No. | | 11 | 12 | 13 | 14 | 15 | 16 | 17 |
|---|---|---|---|---|---|---|---|---|
| Elvax 3689.3 | | 234 | 234 | 234 | 234 | 234 | 234 | 234 |
| Agerite Resin D | | 1.2 | 1.2 | 1.2 | 1.2 | 1.2 | 1.2 | 1.2 |
| PCL 700 | | 23.4 | 23.4 | 23.4 | 23.4 | 23.4 | 23.4 | 23.4 |
| Aerosil 200 coated filler | A | 15.6 | — | — | — | — | — | — |
| | B | — | 15.6 | — | — | — | — | — |
| | C | — | — | 15.6 | — | — | — | — |
| | D | — | — | — | 15.6 | — | — | — |
| | E | — | — | — | — | 15.6 | — | — |
| | F | — | — | — | — | — | 15.6 | — |

-continued

| Formulation No. | 11 | 12 | 13 | 14 | 15 | 16 | 17 |
|---|---|---|---|---|---|---|---|
| G | — | — | — | — | — | — | 15.6 |

The treated silica fillers were prepared as follows. 100 g. Aerosil 200 (surface area approx. 200 m²/g) + 3 g. of silane were mixed in 20 mls methylated spirits. The mixture was tumbled for 1½ hours and then the filler placed in an oven at 100°C for 1 hour. The silanes used were as follows:

A. N-β-(amino ethyl)-γ-aminopropyltrimethoxysilane
B. vinyltris(2-methoxy ethoxy)silane
C. Y-2525 from Union Carbide
D. β-(3,4-epoxy-cyclohexyl)ethylmethoxysilane
E. Y-2384 from Union Carbide
F. Bis(hydroxy ethyl)-γ-aminopropyltriethoxysilane
G. Vinyltriethoxysilane The compounded fillers were then used as above and the adhesives obtained were used to bond crosslinked medium density polyethylene to itself. The following peel strengths were obtained.

| Formulation No. | 23°C | 70°C |
|---|---|---|
| 11 | 59.6 | 20.6 |
| 12 | 55.6 | 25.1 |
| 13 | 49.6 | 34.2 |
| 14 | 72 | 26.7 |
| 15 | 61.6 | 19.8 |
| 16 | 69.6 | 18.7 |
| 17 | 51.0 | 21.2 |

Thus it can be seen that all the treated fillers gave higher bond strengths than formulation 10 which contained an untreated filler and formulation 8 which contained no filler at all.

EXAMPLE 4

| Formulation No. | 18 | 19 | 20 | 21 | 22 | 23 |
|---|---|---|---|---|---|---|
| 1) Elvax 3689.4 | 234 | 234 | — | — | — | — |
| 2) Elvax 3649.4 | — | — | 234 | 234 | — | — |
| 3) Elvax 4260 | — | — | — | — | 234 | 234 |
| PCL 700 | 23.4 | 23.4 | 23.4 | 23.4 | 23.4 | 23.4 |
| Agerite Resin D | 1.2 | 1.2 | 1.2 | 1.2 | 1.2 | 1.2 |
| Aerosil R972 | 15.6 | — | 15.6 | — | 15.6 | — |

1. Elvax 3689.4 is an ethylene vinyl acetate organic acid terpolymer, containing 3 – 4% by weight of acid, to give an acid number of 21, together with 18% by weight of vinyl acetate. The melt flow index was 2.5 and the polymer was manufactured by DuPont.

2. Elvax 3649.4 is a similar polymer containing 20% by weight vinyl acetate, 1.5% of acid to an acid number of 9, and a melt flow index of 6.

3. Elvax 4260 is a similar polymer containing about 28% by weight of vinyl acetate, an acid number of about 6 and a melt flow index of 6.

These adhesives were prepared and used to bond crosslinked medium density polyethylene to itself. The following peel strengths were obtained:

| Formulation No. | 23°C | 70°C |
|---|---|---|
| 18 | 53 | 12.6 |
| 19 | 28 | 4.3 |
| 20 | 59 | 8.03 |
| 21 | 39 | 3.1 |
| 22 | 70 | 5.24 |
| 23 | 18.4 | 2.1 |

EXAMPLE 5

In this Example, the use of different proportions of fillers in various different α-olefin copolymers is illustrated.

| Formulation No. | 24 | 25 | 26 | 27 | 28 | 29 |
|---|---|---|---|---|---|---|
| Elvax 3689.3 | 234 | 234 | 234 | 234 | 234 | 234 |
| PCL 700 | 23.4 | 23.4 | 23.4 | 23.4 | 23.4 | 23.4 |
| Agerite Resin D | 1.2 | 1.2 | 1.2 | 1.2 | 1.2 | 1.2 |
| Aerosil R972 | 0 | 6.3 | 15.6 | 25 | 37.5 | 50 |

These adhesives were prepared as already described and used to bond crosslinked medium density polyethylene to itself. The following peel strengths were obtained.

| Formulation No. | 23°C | 70°C |
|---|---|---|
| 24 | 39 | 18.1 |
| 25 | 30 | 22.7 |
| 26 | 72 | 43.4 |
| 27 | 44 | 24 |
| 28 | 50 | 20.5 |
| 29 | 42 | 20.3 |

| Formulation No. | 30 | 31 | 32 | 33 |
|---|---|---|---|---|
| Elvax 460 | 156 | 156 | 156 | 156 |
| PCL 700 | 15.6 | 15.6 | 15.6 | 15.6 |
| Agerite Resin D | 0.8 | 0.8 | 0.8 | 0.8 |
| Aerosil R972 | 0 | 17 | 34 | 45 |

Elvax 460 is a copolymer of ethylene and 18% vinyl acetate with a melt flow index of 2.5.

These formulations were prepared as described before. The peel strengths obtained were:

| Formulation No. | 23°C | 70°C |
|---|---|---|
| 30 | 69 | 1.7 |
| 31 | 66 | 5.7 |
| 32 | 42 | 5.5 |
| 33 | 40 | 4.1 |

| Formulation No. | 34 | 35 | 36 | 37 |
|---|---|---|---|---|
| 1) Elvax 4260 | 100 | 100 | 100 | 100 |
| 2) DPD 6169 | 50 | 50 | 50 | 50 |
| Aerosil R972 | 0 | 10 | 25 | 50 |
| Agerite Resin D | 0.75 | 0.75 | 0.75 | 0.75 |
| Partially hydrolysed Silane A1111 | 2.4 | 2.4 | 2.4 | 2.4 |

1. Elvax 4260 is an ethylene vinyl acetate methacrylic acid terpolymer, containing about 28% vinyl acetate, with a melt flow index of 6 and sufficient acid to give an acid number of about 6.

2. DPD 6169 is an ethylene-ethyl acrylate copolymer containing 18% of ethyl acrylate, made and sold by Union Carbide.

The formulations were prepared as described and used to bond crosslinked medium density polyethylene to itself. The following peel strengths were obtained.

| Formulation No. | 70°C |
|---|---|
| 34 | 0.74 |
| 35 | 1.3 |
| 36 | 1.8 |
| 37 | 3.5 |

It will be noted that, in general, enhanced peel strengths were obtained over the large range of filler proportions tested. However, increased levels of filler may stiffen the adhesive and reduce its flow and wetting properties, accordingly the optimum filler level may depend on the intended use. Similarly, it will be noted that the optimum filler level may vary from polymer to polymer.

EXAMPLE 6

This Example illustrates the use of various other α-olefin copolymers.

| Formulation No. | 38 | 39 | 40 | 41 | 42 | 43 |
|---|---|---|---|---|---|---|
| 1) EMMA | 100 | 100 | — | — | — | — |
| 2) EMA | — | — | 100 | 100 | — | — |
| 3) DPD 9169 | — | — | — | — | 100 | 100 |
| Agerite Resin D | 0.75 | 0.75 | 0.75 | 0.75 | 0.75 | 0.75 |
| Aerosil R972 | — | 10 | — | 10 | — | 10 |

1. The EMMA polymer was an ethylene-methyl methacrylate copolymer, containing about 15% of methyl methacrylate and having a melt flow index of 10.
2. The EMA was an ethylene-methyl acrylate copolymer containing about 20% of methyl acrylate and having a melt flow index of 5.
3. The DPD 9169 is an ethylene-ethyl acrylate copolymer containing about 18% of ethyl acrylate and having a melt flow index of 20.

These materials were used to bond crosslinked medium density polyethylene to itself. The peel strengths were measured as before.

| Formulation No. | 70°C |
|---|---|
| 38 | 5 |
| 39 | 12 |
| 40 | 3 |
| 41 | 6 |
| 42 | 10 |
| 43 | 31 |

EXAMPLE 7

This Example illustrates the use of graft copolymers as the polar α-olefin component.

| Formulation No. | 44 | 45 | 46 | 47 | 48 | 49 |
|---|---|---|---|---|---|---|
| DPD 9169 | 100 | 100 | — | — | — | — |
| Elvax 4320 | — | — | 75 | 75 | 75 | 75 |
| Elvax 4260 | — | — | 75 | 75 | 75 | 75 |
| Elvax 40 | — | — | 20 | 20 | 20 | 20 |
| Agerite Resin D | 0.75 | 0.75 | 1.0 | 1.0 | 1.0 | 1.0 |
| 1) PK 251 | 5 | 5 | 30 | 30 | 30 | 30 |
| Itaconic acid | 5 | 5 | 5 | 5 | — | — |
| Mono methyl itaconate | — | — | — | — | 5 | 5 |
| t-butyl peroctoate | 2 | 2 | 3 | 3 | 3 | 3 |
| Aerosil R972 | — | 10 | — | 10 | — | 10 |

1. PK 251 is an adhesive promoting additive made from formaldehyde and methyl ethyl ketone, made and sold by Union Carbide Corporation.

The above formulations were milled at about 90°C and the peroxide added last, after the itaconic acid or ester. After addition of all components milling was continued long enough to decompose the peroxide and effect grafting of the monomer to the polymer. The mill nip was closed down and the hide taken off as a thin sheet approximately 15 thousandths of an inch thick. These films were then used to bond crosslinked, flame-retarded low density polyethylene to aluminium sheet which had been degreased with trichloroethylene and etched with chromic acid. The bonds were made as already described.

The peel strengths were measured and found to be:

| Formulation No. | Room Temperature |
|---|---|
| 44 | 38 |
| 45 | 55 |
| 46 | 43 |
| 47 | 66 |
| 48 | 50 |
| 49 | 62 |

Similar results would be expected from the grafting on of maleic and fumaric acid or ester components.

I claim:
1. An adhesive comprising:
   a. a polar copolymer of an α-olefin, and
   b. a filler in an amount of up to about 20% by weight based on the total weight of the adhesive, said filler comprising an inorganic silicon compound containing the Si-O-Si group which has been treated with trimethylchlorosilane.
2. An adhesive as claimed in claim 1, which contains from 3 to 10% by weight of component (b).
3. An adhesive as claimed in claim 1, wherein component (a) is a ethylene copolymer.
4. An adhesive as claimed in claim 3, wherein the ethylene copolymer is an ethylene/vinyl acetate/carboxylic acid terpolymer.
5. An adhesive as claimed in claim 4, wherein component (a) is an ethylene (83%)/vinyl acetate 12%/methacrylic acid terpolymer.
6. An adhesive as claimed in claim 3, wherein component (a) is a copolymer of ethylene and an olefinically unsaturated carboxylic acid or ester thereof.
7. An adhesive as claimed in claim 3, wherein component (a) is an ethylene/vinyl acetate copolymer.
8. An adhesive as claimed in claim 1, wherein component (a) is a graft copolymer.
9. An adhesive as claimed in claim 1, wherein component (a) has an acid number in the range of from 4 to 40.

10. An adhesive as claimed in claim 8, wherein component (a) has an acid number in the range of from 20 to 40.

11. An adhesive as claimed in claim 1, wherein component (a) has a melt flow index of not more than 10.

12. An adhesive as claimed in claim 10, wherein component (a) has a melt flow index of not more than 5.

13. An adhesive as claimed in claim 1, wherein said inorganic silicon compound in component (b) is a silica having a specific surface area of about 200 m²/g.

14. An adhesive as claimed in claim 1, which also comprises one or more other polymeric components to improve the flow properties.

15. An adhesive as claimed in claim 14, wherein a polycaprolactone polymer is included to improve the flow properties.

16. An adhesive as claimed in claim 1, which also comprises one or more additive from pigments, antioxidants, processing aids, adhesion promoters and tackifying resins.

17. An adhesive as claimed in claim 1, wherein the specific surface area of said inorganic silicon compound is at least about 50 m²/g.

18. An adhesive as claimed in claim 17, wherein the specific surface area of said inorganic silicon compound is at least about 100 m²/g.

* * * * *